US006391318B1

(12) United States Patent
Illum et al.

(10) Patent No.: US 6,391,318 B1
(45) Date of Patent: May 21, 2002

(54) VACCINE COMPOSITIONS INCLUDING CHITOSAN FOR INTRANASAL ADMINISTRATION AND USE THEREOF

(75) Inventors: Lisbeth Illum, Nottingham; Steven Neville Chatfield, Berkshire, both of (GB)

(73) Assignee: West Pharmaceutical Services Drug Delivery & Clinical Research Centre Limited, Nottingham (GB)

(*) Notice: Subject to any disclaimer, the term of this patent is extended or adjusted under 35 U.S.C. 154(b) by 0 days.

(21) Appl. No.: 09/088,185

(22) Filed: Jun. 1, 1998

Related U.S. Application Data

(63) Continuation of application No. PCT/GB96/03019, filed on Dec. 9, 1996.

(30) Foreign Application Priority Data

Dec. 7, 1995 (GB) ............................................ 9525083

(51) Int. Cl.[7] ................................................ A61K 47/00

(52) U.S. Cl. ............................... 424/278.1; 424/206.1; 424/240.1; 514/55

(58) Field of Search ....................................... 424/278.1

(56) References Cited

U.S. PATENT DOCUMENTS

| | | | | | |
|---|---|---|---|---|---|
| 4,950,740 | A | * | 8/1990 | Greenfield et al. | 530/350 |
| 5,554,388 | A | * | 9/1996 | Illum | 424/501 |
| 5,629,011 | A | * | 5/1997 | Illum | 424/434 |
| 5,912,000 | A | * | 6/1999 | Podolski et al. | 424/278.1 |
| 6,048,536 | A | | 4/2000 | Chatfield | |

FOREIGN PATENT DOCUMENTS

| | | |
|---|---|---|
| EP | 0 460 020 B2 | 12/1991 |
| EP | 0 183 556 A2 | 6/1996 |
| WO | WO 90/09780 A1 | 9/1990 |
| WO | WO 96/09805 A2 | 4/1996 |
| WO | WO 96/10421 A1 | 4/1996 |
| WO | WO 97/16208 A1 | 5/1997 |

OTHER PUBLICATIONS

Aspden, T.J., et al., 1995, "Chitosan as a nasal delivery system: Evaluation of the effect of chitosan on mucociliary clearance rate in the frog palate model", Internat. J. Pharmaceut. 122:69–78.*

Polk, A.E., et al., 1994, "Oral delivery in aquaculture: controlled release of proteins from chitosan–alginate microcapsules", Aquacult. Engineer. 13:311–323.*

Illum, L., et al., 1994, "Chitosan as a novel nasal delivery system for peptide drugs", Pharmaceut. Res. 11(8):1186–1189.*

Cahill, et al., "Mice are protected against *Bordetella pertussis* infection by intra–nasal immunization with filamentous haemagglutinin," *FEMS Microbiology Letters* 107:211–16 (1993).

de Haan, et al., "Mucosal immunoadjuvant activity of liposomes: induction of systemic IgG and secretory IgA responses in mice by intranasal immunization with an influenza subunit vaccine and coadministered liposomes," *Vaccine* 13(2):155–62 (1995).

Hibberd, et al., "Immunization Strategies for the Immunocompromised Host: The Need for Immunoadjuvants," *Ann. Intern. Med.* 110:995–56 (1989).

Nishimura, et al., "Adjuvant activity of chitin derivatives in mice and guinea–pigs," *Vaccine* 3(5):379–84 (1985).

Oka, et al., "Enhancing effects of pertussis toxin B oligomer on the immunogenicity of influenza vaccine administered intranasally," *Vaccine* 12(14):1255–58 (1994).

* cited by examiner

*Primary Examiner*—Laurie Scheiner
*Assistant Examiner*—Jeffrey S. Parkin
(74) *Attorney, Agent, or Firm*—Akin, Gump, Strauss, Hauer & Feld, L.L.P.

(57) ABSTRACT

A variety of different types of nasal vaccine systems have been described including cholera toxin, microspheres, nanoparticles, liposomes, attenuated virus, and outer membrane proteins (proteosomes). The present invention is directed toward a novel nasal vaccine composition that utilizes the cationic polysaccharide, chitosan, as a delivery system. Chitosan is a polysaccharide comprising copolymers of glucosamine and N-acetylglucosamine. The term chitosan encompasses a series of chitosan polymers with different molecular weights (50 kDa–2,000 kDa) and degree of acetylation (40%–98%). Several vaccine animal studies were carried out employing influenza or pertussis antigens in combination with chitosan. Nasal administration of chitosan-antigen nasal vaccines induced significant serum IgG responses and secretory IgA levels. Animals vaccinated via the nasal route with various chitosan-antigen vaccines were also found to be protected against the appropriate challenge.

17 Claims, 6 Drawing Sheets

VACCINE COMPOSITIONS INCLUDING CHITOSAN FOR INTRANASAL ADMINISTRATION AND USE THEREOF

This is a continuation under 37 C.F.R. § 1.53(b) of PCT/GB96/03019, filed Dec. 9, 1996, which claims priority to GB 9525083.3, filed Dec. 7, 1995.

BACKGROUND OF THE INVENTION

The invention is generally in the field of vaccine compositions, and specifically those for intranasal administration.

Vaccines are preparations of antigenic materials, administered to recipients with a view to enhancing resistance to infection by inducing active immunity to specific microorganisms, for example bacteria or viruses.

Vaccines, which may be as single or mixed component vaccines, are presented in a variety of forms. For example, current influenza vaccines consist of either inactivated whole virus, disrupted virus (split vaccines) or purified preparations of antigenic proteins.

Vaccines are typically administered parenterally via injections. Traditional parenteral immunisation regimes are known to have a number of drawbacks. For example, many individuals possess a natural fear of injections and may experience psychological discomfort as a result. Furthermore, many individuals find injections physically uncomfortable. Moreover, parenteral vaccination (e.g. intramuscular, sub-cutaneous etc.) is not an effective means of eliciting local antibody production if there has been no previous local exposure (e.g. by way of infection).

An effective local and/or topical administration regime is therefore desirable.

In the case of some diseases, it would be advantageous to stimulate the mucosal immune system. In order to do this, the vaccine must be applied topically to a mucosal surface. Thus, in certain cases (e.g. in the case of infections of the upper respiratory tract), it would be beneficial to obtain more effective stimulation of the local mucosal immune system of the respiratory tract.

Accordingly, a number of attempts have been made to develop mucosal vaccines. One drawback, however, is that inactivated vaccines are often poorly immunogenic when given mucosally. In order to overcome this problem, different approaches to improving the immunogenicity of vaccines given orally or intranasally have included the use of adjuvants (see below), encapsulation of the vaccine in a variety of microspheres, and the use of live attenuated strains.

Certain adjuvants have been shown, when co-administered with vaccine antigens, to further boost the effectiveness of vaccine compositions by stimulating the immune response (see e.g. Hibberd et al, *Ann. Intern. Med.*, 110, 955 (1989)). Examples of adjuvants which have been shown to be effective include interferon alpha, *Klebsiella pneumoniae*, glycoprotein and interleukin-2.

Chitosans are derivatives of chitin or poly-N-acetyl-D-glucosamine in which the greater proportion of the N-acetyl groups have been removed through hydrolysis.

European Patent Application 460 020 discloses pharmaceutical formulations including chitosans as mucosal absorption enhancers. That the chitosan could provide an adjuvant effect when administered in a vaccine composition is neither disclosed nor suggested.

SUMMARY OF THE INVENTION

Provided are vaccine compositions for intranasal administration, which compositions include one or more antigen and an effective adjuvant. Also provided are methods of immunizing a mammal against diseases by administering such compositions to the mammal, methods of enhancing the immunogenicity of intranasally administered antigens, and uses of antigens in combination with an adjuvant for the manufacture of a vaccine composition for intranasal administration to immunize a mammal against specific diseases.

BRIEF DESCRIPTION OF THE DRAWINGS

FIG. 3*a* uses a log scale, while FIG. 3*b* uses a linear scale.

DETAILED DESCRIPTION OF THE INVENTION

Figure 1:
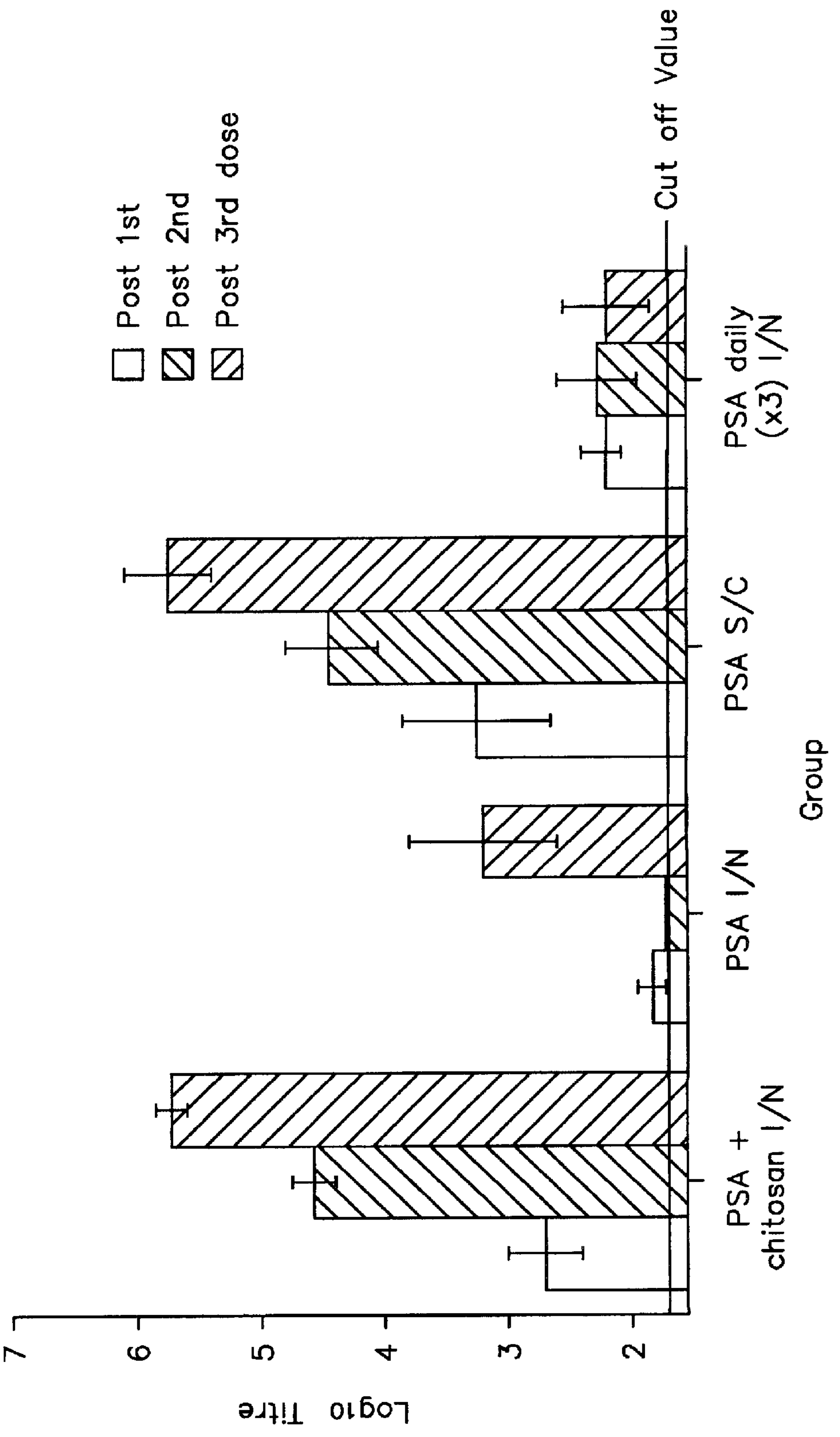
FIG. 1 illustrates the serum IgG anti-haemagglutinin response in mice immunized with purified surface antigen of influenza (PSA). Each bar represents the geometric mean titre of four mice. The error bars represent 1 standard error of the mean. The cut-off value is 50 which is the lower limit of detection.

It has now been found that, upon intranasal co-administration, chitosan enhances the immune response of antigens and thus provides an adjuvant effect.

Accordingly, in a first aspect of the invention, there is provided a vaccine composition adapted for intranasal administration, which composition includes antigen and an effective adjuvant amount of a chitosan (hereinafter referred to as "the compositions according to the invention").

The term "effective adjuvant amount" will be well understood by those skilled in the art, and includes an amount of a chitosan which is capable is of stimulating the immune response to nasally administered antigens, i.e. an amount that increases the immune response of a nasally administered antigen composition, as measured in terms of the IgA levels in the nasal washings. Suitably effective increases in IgA levels include by more than 5%, preferably by more than 25%, and in particular by more than 50%, as compared to the same antigen composition without any adjuvant.

Preferred concentrations of the chitosan in the compositions according to the invention are in the range 0.02 to 10%, more preferably 0.1 to 5% and particularly 0.25% to 2%.

It has now been found that, by administration of an antigen together with a particular chitosan derivative in an intranasal composition, it is possible to achieve an immune (e.g. IgG and IgA) response. It has now been found that, if a chitosan is incorporated into intranasal vaccine compositions containing an antigen, good systemic and local immune responses are produced. In particular, it has been found that the intranasal administration of the compositions according to the invention enhances both a protective IgA mucosal immune response and an IgG systemic immune response.

Thus, the invention further provides a method of enhancing a protective IgA mucosal immune response and an IgG systemic immune response by administering intranasally to a mammal a vaccine composition including an antigen and an effective adjuvant amount of a chitosan.

The antigen may be provided as a sub-unit of a cell wall protein or polysaccharide, or as DNA which produces the antigen in the cells after introduction of the DNA (e.g. by transfection). Strictly speaking, the DNA is not itself an "antigen" but it encodes the antigen and is termed antigen herein.

The antigen may further be provided in a purified or an unpurified form. However, the antigen preferably is provided in a purified form.

Antigens of the compositions and methods disclosed herein may include proteins from pathogens, recombinant proteins, peptides, polysaccharides, glycoproteins, lipopolysaccharides and DNA molecules (polynucleotides).

The following list of antigens is provided by means of illustration and is not meant to be exclusive: influenza virus antigens (such as haemagglutinin and neuraminidase antigens), *Bordetella pertussis* antigens (such as pertussis toxin, filamentous haemagglutinin, pertactin), human papilloma virus (HPV) antigens, *Helicobacter pylori* antigens, rabies antigens, tick-borne encephalitis (TBE) antigens, meningococcal antigens (such as capsular polysaccharides of serogroup A, B, C, Y and W-135), tetanus antigens (such as tetanus toxoid), diphtheria antigens (such as diphtheria toxoid), pneumococcal antigens (such as *Streptococcus pneumoniae* type 3 capsular polysaccharide), tuberculosis antigens, human immunodeficiency virus (HIV) antigens (such as GP-120, GP-160), cholera antigens (such as cholera toxin B subunit), staphylococcal antigen (such as staphylococcal enterotoxin B), shigella antigens (such as shigella polysaccharides), vesicular stomatitis virus antigen (such as vesicular stomatitis virus glycoprotein), cytomegalovirus (CMV) antigens, hepatitis antigens (such as hepatitis A (HAV), B (HBV), C (HCV), D (HDV) and G (HGV) virus antigens), respiratory syncytial virus (RSV) antigens, herpes simplex antigens, or combinations thereof (e.g. combinations of diphtheria, pertussis and tetanus (DPT)). Suitable antigens also include those delivered for induction of tolerance, such as retinal antigens.

Preferred antigens include *Bordetella pertussis* antigens, meningococcal antigens, tetanus antigens, diphtheria antigens, pneumococcal antigens, tuberculosis antigens and RSV antigens.

According to a further aspect of the invention, the antigen preferably is not an influenza virus antigen.

Preferably, the chitosan is water-soluble, and may advantageously be produced from chitin by deacetylation to a degree of greater than 40%, preferably between 50% and 90%, and more preferably between 70% and 95%, deacetylation.

Particular deacetylated chitosans which may be mentioned include the SEA CURE™ chitosan glutamate available from Protan Biopolymer A/S, Drammen, Norway.

The molecular weight of the chitosan may be between 10 kD and 500 kD, preferably between 50 kD and 300 kD and more preferably between 100 kD and 300 kD.

The compositions according to the invention may be used in the immunisation of a host against diseases, for example as described in the tests below.

According to a further aspect of the invention, there is provided a method of immunising a host against infection by disease, which method comprises administering intranasally to the host a vaccine composition comprising antigen together with an effective adjuvant amount of a chitosan as hereinbefore defined.

Moreover, according to a further aspect of the invention, there is provided a method of enhancing the immune response of an intranasally administered antigen, which method comprises co-administration of said antigen and a chitosan as hereinbefore defined.

The intranasal compositions according to the invention can be formulated as liquids or dry powders, for administration as aerosols, drops or insufflations.

Preferably, the compositions according to the invention are formulated as dry powders or in the form of microspheres.

Compositions for administration as nasal drops may contain one or more excipients of the type usually included in such compositions, for example preservatives, viscosity adjusting agents, tonicity adjusting agents, buffering agents and the like.

In order to ensure that the chitosan remains soluble in an aqueous medium, and to ensure also that the antigen is not adversely affected by too acidic a pH, a solution for intranasal administration preferably has a pH in the range 5.5 to 6.5, most preferably approximately pH 6.

Also provided is a means for dispensing the intranasal compositions of purified surface antigen and chitosan. A dispensing device may, for example, take the form of an aerosol delivery system, and may be arranged to dispense only a single dose, or a multiplicity of doses.

The vaccine should be administered to the patient in an amount effective to stimulate a protective immune response in the patient. For example, the vaccine may be administered to humans in one or more doses, each dose containing 1–250 micrograms and more preferably 2–50 micrograms of protein or polysaccharide antigen prepared from each viral or bacterial strain. For example, where haemagglutinin and neuraminidase preparations are prepared from three virus strains, e.g. 2×Influenza A and 1×Influenza B, a total dose of viral protein administered may be in the range 15–150 micrograms. Where *Bordetella pertussis* antigens are employed, a total dose of bacterial protein administered as FHA, pertussis toxin (toxoid) or pertactin, either individually or in combination may be in the range 5–150 micrograms.

The invention is illustrated, but in no way limited, by the following examples. The studies described clearly indicate that chitosan used as an adjuvant for mucosal vaccination, has the potential for enhancing both systemic and mucosal humoral responses to a number of antigens.

EXAMPLE 1

Preparation of Influenza B Purified Surface Antigen/chitosan Glutamate Composition 1A. A solution of 1% chitosan glutamate, a medium viscosity deacetylated chitin having approximately 11% residual N-acetyl groups, was prepared by dissolving the chitosan glutamate in 0.8% sodium chloride. The grade of chitosan glutamate used was SEA CURE+210™, available from Protan Biopolymer A/S, Drammen, Norway.

1B. Influenza purified surface antigen (PSA) containing both Influenza A and Influenza B protein, commercially available from Evans Medical Limited, Speke, Merseyside, United Kingdom, under the Trade Mark FLUVIRIN™, was made up in phosphate buffered saline to give a protein concentration of approximately 1 mg/ml. The PSA consists almost entirely of the spike protein haemagglutinin (HA), although it does contain some neuraminidase.

1C. A 1:1 mixture of the chitosan glutamate solution and the PSA solution was prepared to give an intranasal vaccine composition containing 0.5% chitosan glutamate (11% acetylated), 0.8% NaCl, 0.05% PSA and phosphate buffer to give a solution pH of 6.

1D. Control solutions containing the same concentrations of PSA but not chitosan glutamate, and the same concentrations of chitosan glutamate but no PSA, were also prepared. In addition, a composition comprising the same concentration of PSA adsorbed on to the known adjuvant Alhydrogel (aluminum hydroxide) was prepared. The PSA was adsorbed on to the Alhydrogel overnight at 40° C.

EXAMPLE 2

Mice Immunisation Studies

2A. The four compositions prepared as described in Example 1 were administered to groups of twelve adult (6–8 weeks) female BALB/c mice as follows:

Group 1: 20 μl (10 μl per nostril) PSA/chitosan solution administered intranasally. PSA dose=10 μg.

Group 2: 20 μl PSA administered intranasally (total PSA dose=10 μg).

Group 3: 200 μl PSA/Alhydrogel administered subcutaneously (PSA dose=10 μg)

Group 4: 20 μl chitosan solution administered intranasally.

Group 5: 20 μl PSA (10 μl per nostril) administered daily for three days. (Groups of four mice employed for this study).

2B. The immunisation procedure was carried out three times at monthly intervals, with the exception of Group 5 where the mice were immunised with three successive daily doses. The immunisation and sampling regime is shown in Table 1.

TABLE 1

| Immunisation | Day | Sample | Day |
|---|---|---|---|
| 1 | 1 | 1 | 21 |
| 2 | 30 | 2 | 44 |
| 3 | 57 | 3 | 71 + 72 |

Immunisation and Sampling Regime

At each sampling point four mice from each group were terminally bled by cardiac puncture, their heads were removed and their nasal passages lavaged with 1 ml PBS+1% bovine serum albumin. Group 5 contained four mice only so blood was obtained by tail puncture for the first two samples and nasal washes were only performed at the third sampling point.

Antibody Assays

In all assays whole influenza vaccine (WIV) was used as antigen. Although WIV is only about 50% HA the assays were thought to be measuring primarily anti-HA antibodies. This assumption was confirmed by substituting PSA (100% HA) for WIV and repeating some assays. The results were similar with either antigen. HA-specific serum IgG and nasal IgA antibodies were measured by Enzyme Linked Immunosorbant Assay (ELISA). After correcting for background, the individual optical density (OD) dilution curves were plotted and the titre values determined. The titre was determined as the dilution of serum that gave an OD reading of 0.2 or the dilution of nasal wash that gave an OD reading of 0.1.

As well as taking nasal washes at the third sample, lymphocytes were isolated from the mucous membranes of the nasal cavity and the lungs and the local immune response analysed by ELISPOT.

Results

1. Serum anti-HA Serum Response

Purified Surface Antigen (FIG. 1 and Table 2): As expected a good serum response was elicited by subcutaneous (SIC) immunisation with PSA+Alhydrogel. All the animals tested had seroconverted after the primary immunisation and the geometric mean titre (GMT) was good. The response increased after each boost, the GMT after the third dose was very high (about 800,000). In contrast the serum response to PSA alone administered intranasally was poor: only two of four mice had seroconverted after the first dose, none of the mice tested had serum HA antibodies after the second dose (these are separate mice from those tested after the first immunisation) and although all animals tested had seroconverted after the third dose the GMT was lower than that of animals receiving one dose of PSA+Alhydrogel. Chitosan enhanced the serum response of intranasally administered PSA; after the third vaccination the antibody response in mice that received PSA+chitosan was 360-fold greater than that of mice receiving PSA alone I/N. The magnitude of the serum response in the PSA+chitosan mice was very similar to that of SIC immunised mice; in fact there was no statistical difference in the GSAT's of the two groups at any sampling point (Student's t-Test $p>0.01$).

Some mice were immunised three times on successive days with PSA alone administered intranasally to study whether this regime had advantages over the once monthly regime. Although all the mice in this group had detectable serum antibodies 21 days after the first dose and the GMT at this time point was greater than in mice that had received a single dose of PSA intranasally, the number of mice seropositive decreased during the course of the study although the GMT did not (in this group the same mice were sampled at each time point). At the final time point the GMT of the mice on the monthly regime was an order of magnitude greater than mice on the daily regime.

TABLE 2

Serum IgG anti-HA response in PSA immunised mice

| Group | Post-Dose 1 Sero-Convn.[a] | Post-Dose 1 GMT | Post-Dose 2 Sero-Convn. | Post-Dose 2 GMT | Post-Dose 3 Sero-Convn. | Post-Dose 3 GMT |
|---|---|---|---|---|---|---|
| PSA + Chitosan | 4/4 | 557 | 4/4 | 40504 | 4/4 | 653113 |
| PSA I/N | 2/4 | 67 | 0/4 | <50 | 4/4 | 1818 |
| PSA S/C | 4/4 | 2339 | 4/4 | 35196 | 4/4 | 816552 |
| PSA 3 Daily Doses | 4/4 | 182 | 3/4 | 229 | 2/4 | 180 |

[a]No. positive/No. tested

2. Nasal Wash IgA Anti-HA Response

Figure 2:
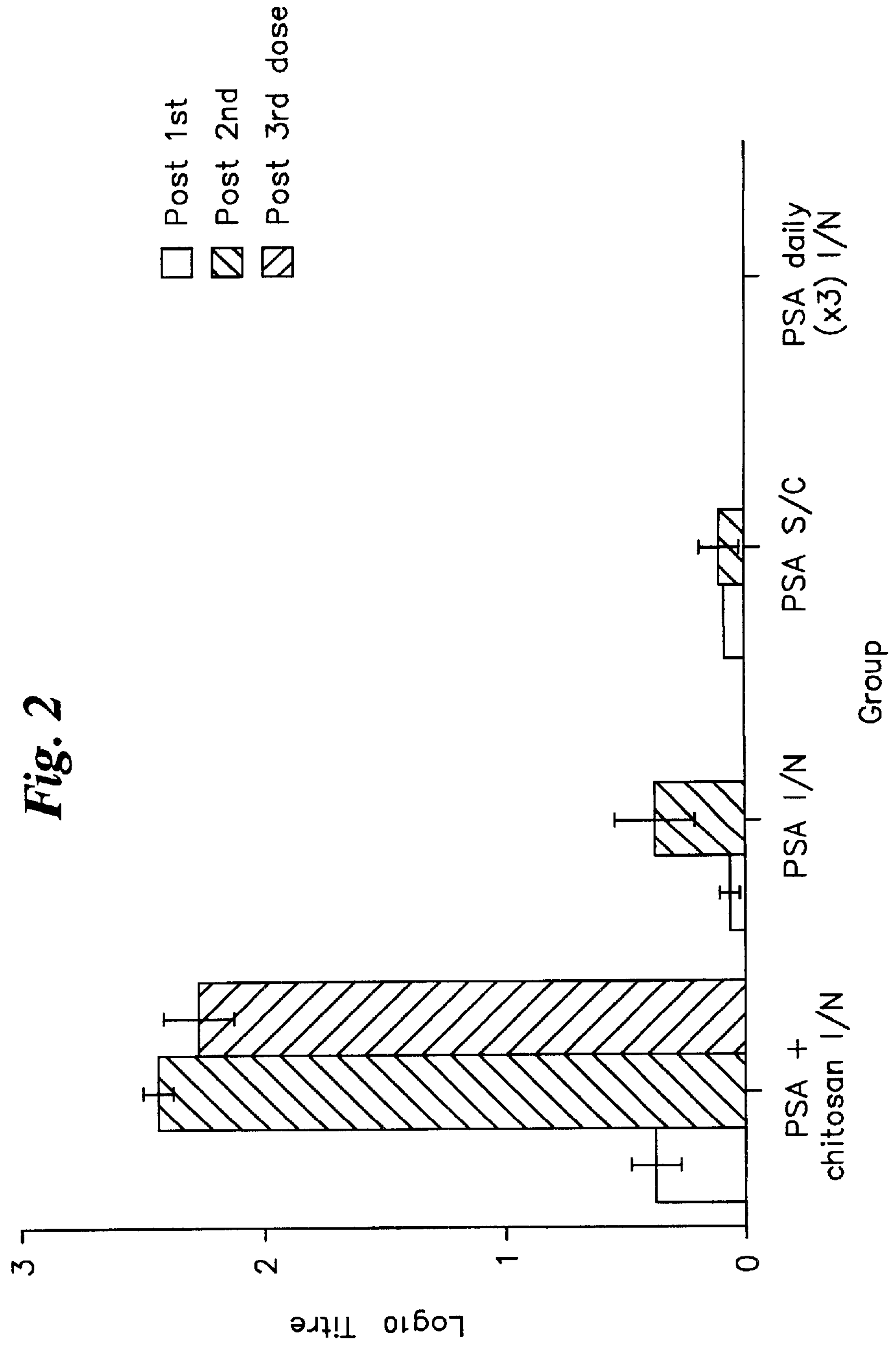
FIG. 2 illustrates the nasal IgA anti-haemagglutinin response in mice immunized with purified surface antigen. As with FIG. 1, each bar represents the geometric mean titre of four mice, and the error bars represent 1 standard error of the mean.

Purified Surface Antigen (FIG. 2 and Table 3): PSA+Alhydrogel given subcutaneously was very poor at inducing a nasal IgA response which is consistent with our previous findings and those of others. PSA alone given intranasally was also a poor mucosal immunogen although it was slightly better than subcutaneous immunisafion in terms of the number of animals responding. Adding chitosan greatly boosted the IgA response, although the response was low after the first dose, HA-specific IgA could be detected in three out of four mice. The IgA response was boosted greatly in these mice by the second immunisation. The final immunisation had little effect; in fact the mean specific IgA levels hard decreased slightly.

TABLE 3

Nasal IgA anti-HA response in PSA immunised mice

| | Post-Dose 1 | | Post-Dose 2 | | Post-Dose 3 | |
|---|---|---|---|---|---|---|
| Group | Mucosal Convn.[a] | GMT | Mucosal Convn. | GMT | Mucosal Convn. | GMT |
| PSA + Chitosan | 3/4 | 2.26 | 4/4 | 282.81 | 4/4 | 184.47 |
| PSA I/N | 0/4 | <1 | 1/4 | 1.20 | 3/4 | 2.31 |
| PSA S/C | 0/4 | <1 | 0/4 | <1 | 2/4 | 1.32 |
| PSA 3 Daily Doses | | | | | 0/4 | <1 |

[a]No. positive/No. tested

Responses to Chitosan Alone

The sera and nasal lavage fluid from the control mice immunised with chitosan alone were negative in all the assays.

Figure 3A:
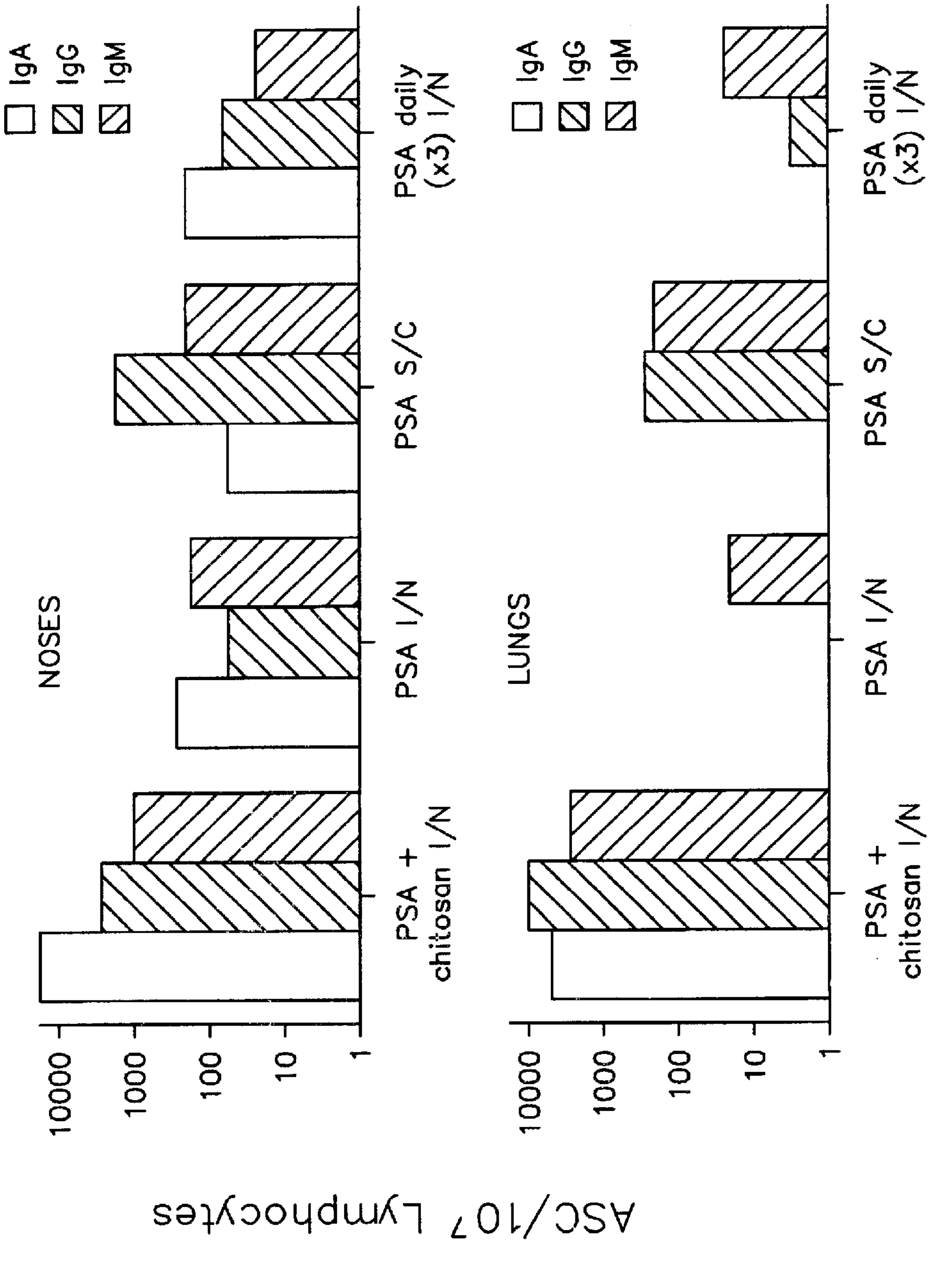
FIGS. 3*a* and 3*b* illustrate the determination of nasal and pulmonary anti-haemagglutinin secreting cells of mice immunized with purified surface antigen (PSA), using ELISPOT.
Figure 3B:
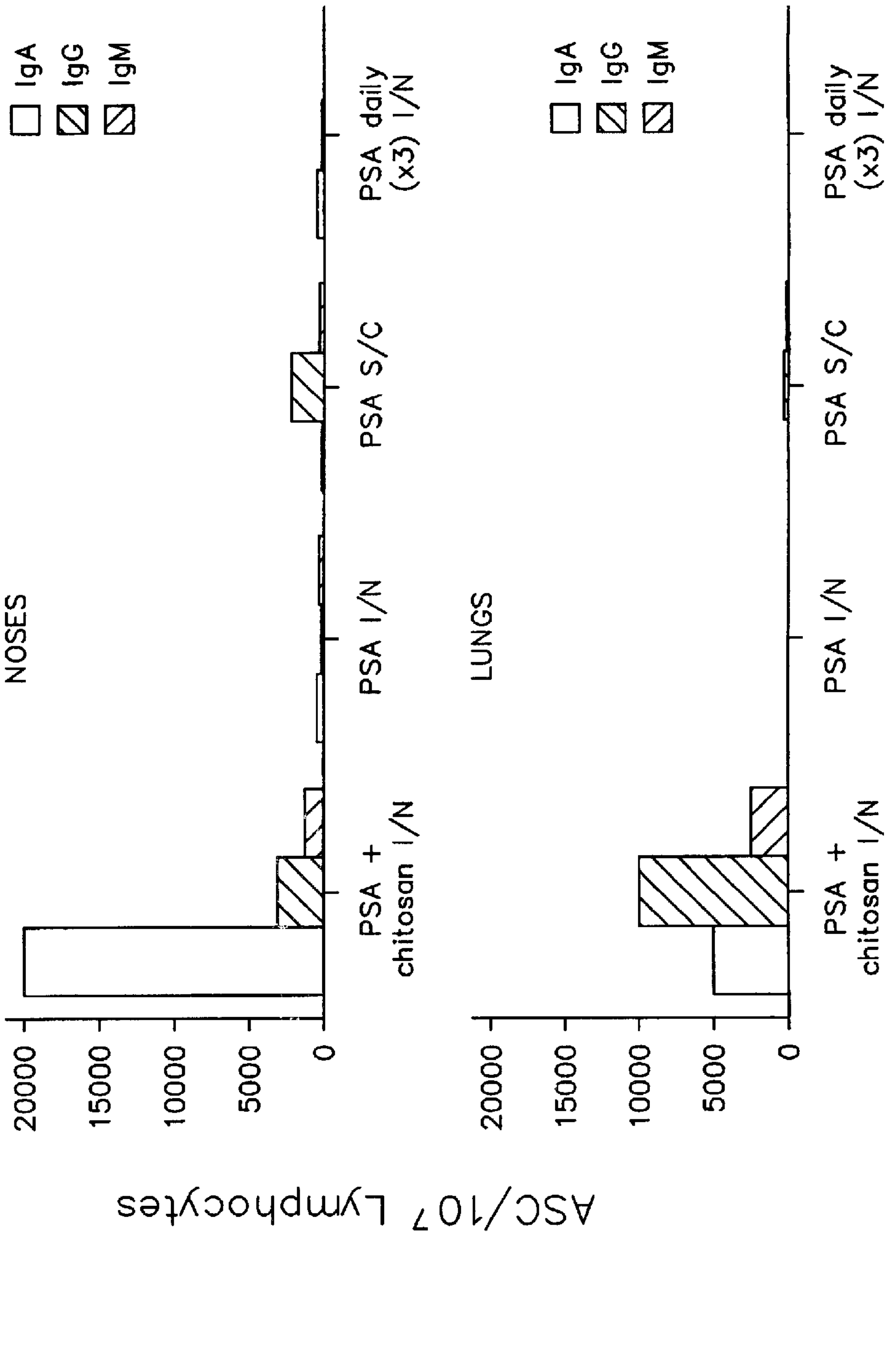

Local Anti-HA Antibody Secreting Cell Response (ASC) in Nasal and Pulmonary Tissues Lymphocytes were isolated from the nasal mucosa and lung parenchyma of groups of four mice at the third sampling point. Lymphocytes from individual mice were pooled and assayed for cells secreting IgA, IgG and IgM anti-flu antibodies using ELISPOT. The results are shown in FIGS. 3*a* and 3*b*.

B cells secreting HA-specific antibodies were detectable in the nasal and lung tissue of all groups. There were far greater numbers of such cells in the PSA+chitosan group and this is most apparent when the results are plotted on a linear scale (FIG. 3*b*). In all cases, except subcutaneously immunised mice, IgA antibody secreting cells (ASC) predominated in the nasal cavity whereas either IgG or IgM predominated in the lungs. The magnitude of the response is similar in the lungs and nose of PSA+chitosan mice.

EXAMPLE 3

Preparation of *Bordetella pertussis* Filamentous Haemagglutinin/chitosan Glutamate Composition 3A. A solution of 1% (10 mg/ml) chitosan glutamate (CSN) was prepared as described in Example 1 above.

3B *Bordetella pertussis* filamentous haemagglutinin (FHA), obtained from the National Institute for Biological Sciences, South Mimms, Potters Bar, London, United Kingdom, was made up in phosphate buffered saline (PBS) to give a protein concentration of approximately 1 mg/ml.

3C A 1:1 mixture of the CSN solution and the FHA solution was prepared to give an intranasal vaccine containing 0.5% CSN, 0.5 mg/ml FHA, 0.8% sodium chloride and phosphate buffer, pH 6.0.

3D Control solution for intranasal vaccination containing the same concentration of FHA but not CSN was also prepared. In addition, a mixture containing approximately 0.1 mg/ml of FHA adsorbed onto the known adjuvant Alhydrogel (aluminum hydroxide) was prepared. The FHA was adsorbed on to Alhydrogel by stirring the mixture for 30 minutes at room temperature.

Mice Immunisation Studies

3E The three compositions prepared as described above (sections 3C and 3D) were administered to groups of 13 adult male Balb/c mice as follows:

Group 1: 20 μl (10 μl per nostril) FHA solution administered intranasally. (FHA dose 10 μg)

Group 2: 20 μl (10 μl per nostril) FHA/CSN solution administered intranasally. (FHA dose=10 μg and chitosan=100 μg)

Group 3: 50 μl FHA/Alhydrogel mixture administered subcutaneously. (FHA dose=5 μg and Alhydrogel=0.25 mg)

Immunisation and Sampling Regime

3D The immunisation procedure was carried out three times at monthly intervals. The immunisation and sampling regime is shown in Table 4.

3E Four mice from each group at sampling points 1 and 2 and five mice from each group at sampling point 3 were terminally bled by cardiac puncture. After collection of blood samples the animals were killed with an intravenous overdose of pentobarbitone sodium and the nasal passages and the lungs were respectively lavaged with 1 ml PBS containing 1% bovine serum albumin.

TABLE 4

| Immunisation | Day | Sample | Day |
|---|---|---|---|
| 1 | 1 | 1 | 21 |
| 2 | 28 | 2 | 42 |
| 3 | 56 | 3 | 70 |

Antibody Analysis

3F Anti-FHA IgG antibodies in the serum samples and anti-FHA secretory IgA antibodies in the nasal wash and lung lavage samples were measured by Enzyme Linked Immunosorbant Assay (ELISA). To compare the antibody response elicited by the different compositions in the individual animals, certain values were assigned to the control positive serum and the control positive lung lavage samples, used for preparing the standard curves during the analysis of the test samples. The control positive serum and the control positive lung lavage were given values of 106 IgG Eq. units/ml and 104 IgA Eq. units/ml respectively.

Results

Figure 4A:
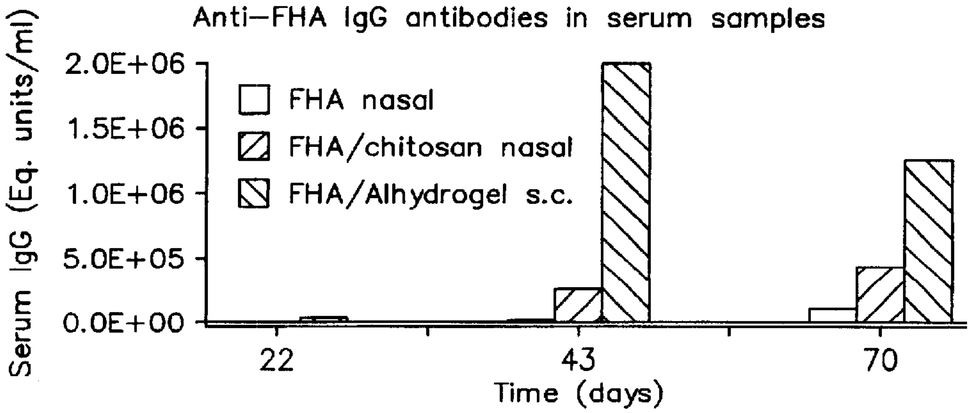
FIGS. 4*a*, 4*b*, and 4*c* illustrate the anti-*Bordetella pertussis* filamentous haemagglutinin (anti-FHA) serum IgG response, the anti-FHA secretory IgA response in lung lavage and the anti-FHA secretory IgA response, respectively, in nasal wash in mice immunized with FHA.

3G The serum IgG concentrations (Table 5 and FIG. 4*a*) show that the nasally administered FHA/chitosan composition elicited a steady increase in response on days 22, 43 and 70. In comparison, the nasally administered FHA solution also elicited some response by Day 70, but this was only one fifth of the corresponding response produced by FHA/chitosan solution. As expected, the subcutaneously administered FHA/Alhydrogel composition elicited a high secondary response (Day 43).

This response was seven times as much as the corresponding response produced by the FHA/chitosan nasal composition. However, the response to subcutaneous administration decreased by Day 70 and this was only three times as much as the corresponding value for the FHA/chitosan nasal composition.

Figure 4B:
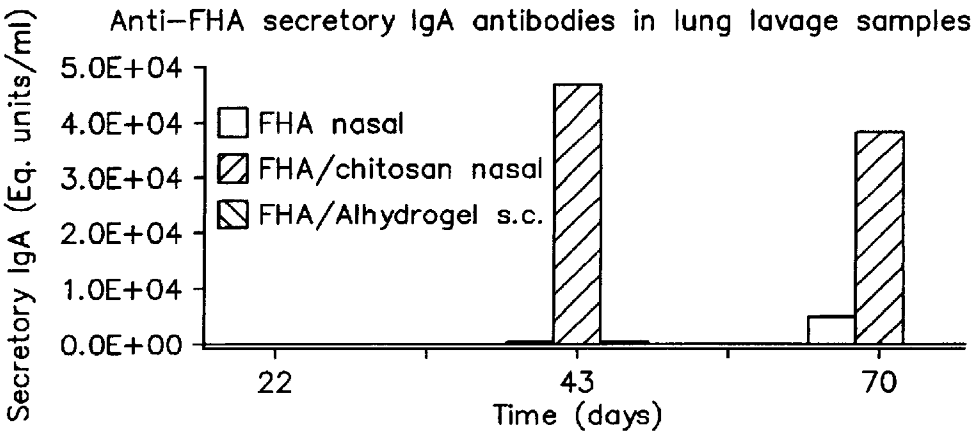

3H The secretory IgA concentrations in the lung lavages (Table 5, FIG. 4*b*) clearly show that the FHA/chitosan nasal composition elicited the most response both on days 43 and 70 as compared to the responses produced by either the nasally administered FHA solution or the subcutaneously administered FHA/Alhydrogel composition. On Day 43 the response was 100 and 250 times as much as the responses elicited by the nasal FHA solution and the subcutaneous FHA/Alhydrogel composition respectively.

Figure 4C:
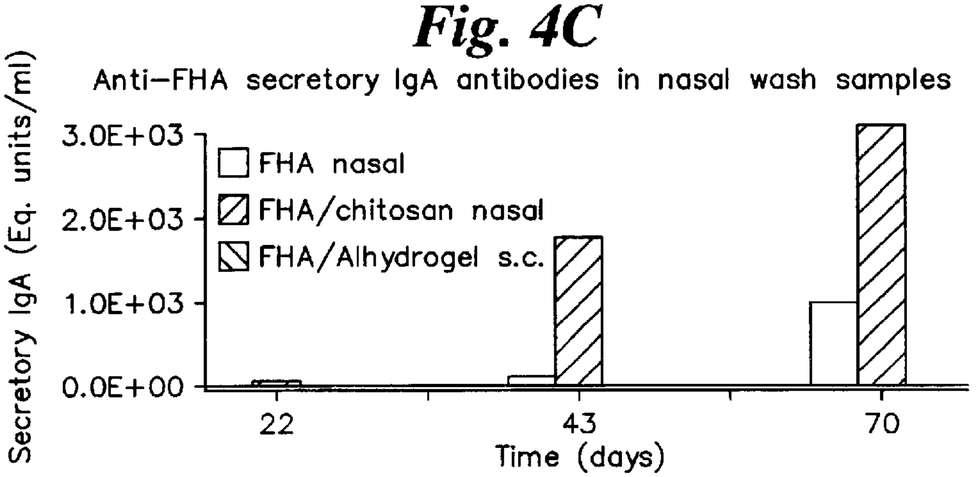

3I The secretory IgA concentrations in the nasal washes (Table 5 and FIG. 4*c*) also show that the FHA/chitosan nasal composition elicited a steady increase in response on days 43 and 70. In comparison the subcutaneous administration produced no response at all, whereas the nasal FHA solution produced some response on Day 70, which was only a third of the response produced by the FHA/chitosan nasal compositions.

ing 0.5% CSN, approximately 100 μg/ml FHA, 100 μg/ml PT, 0.8% sodium chloride and phosphate buffer.

4D A control solution for intranasal vaccination containing the same concentration of FHA and PT but not CSN was prepared. A negative control solution for intranasal vaccination containing 0.5% CSN but neither FHA nor PT was also prepared by diluting one part 2% CSN solution with three parts PBS containing 0.0014 M potassium chloride and 0.3185 M sodium chloride. In addition, a mixture containing approximately 10 μg/ml FHA and 10 μg/ml PT adsorbed onto the known adjuvant Alhydrogel (200~g/ml) was prepared. The antigens were adsorbed on to Alhydrogel by stirring the mixture for 30 min at room temperature.

Mice Immunisation Studies

4E The four compositions prepared as described above (sections 3C and 3D) were administered to groups of 10 adult female Balb/c mice as follows:

TABLE 5

Serum IgG, lung lavage secretory IgA, and nasal wash secretory IgA antibody concentrations after the nasal administration of FHA (10 μg/mouse) either alone or in combination with chitosan in solution formulations and after the subcutaneous administration of FHA (5 μg/mouse) in combination with Alhydrogel in a solution formulation in mice

| | Serum IgG (IgG Eq. units/ml ± SD) | | | Lung lavage IgA (IgA Eq. units/ml ± SD) | | | Nasal wash IgA (IgA Eq. units/ml ± SD) | | |
|---|---|---|---|---|---|---|---|---|---|
| Time after dosing (days) | FHA (nasal) | FHA/chitosan (nasal) | FHA/ Alhydrogel (s.c.) | FHA (nasal) | FHA/chitosan (nasal) | FHA/ Alhydrogel (s.c.) | FHA (nasal) | FHA/chitosan (nasal) | FHA/ Alhydrogel (s.c.) |
| 22 | 242 ± 74.0 | 3167 ± 3621.0 | 30092 ± 9447.2 | 78 ± 56.8 | 28 ± 56.5 | 44 ± 4.2 | 0 | 42 ± 83.2 | 0 |
| Seroconversion | 4 | 4 | 4 | 3 | 1 | 3 | 0 | 1 | 0 |
| 43 | 4311 ± 5912.2 | 257720 ± 59170.6 | 1915684 ± 1706830.7 | 423 ± 507.9 | 46380 ± 57554.3 | 185 ± 219.1 | 124 ± 144.4 | 1657 ± 612.7 | 0 |
| Seroconversion | 4 | 4 | 4 | 4 | 4 | 4 | 2 | 4 | 0 |
| 70 | 92925 ± 162364.3 | 430139 ± 121006.5 | 1230048 ± 687737.1 | 4619 ± 8982.8 | 38006 ± 48405.3 | 87 ± 20.5 | 918 ± 1527.1 | 2868 ± 1503.9 | 0 |
| Seroconversion | 5 | 5 | 5 | 3 | 5 | 5 | 2 | 5 | 0 |

NOTE:
For control IgG assume: 1 000 000 IgG Eq. units/ml
For control IgA assume: 10 000 IgA Eq. units/ml
Number of samples analysed per formulation for days 22 and 43 were 4
Number of samples analysed per formulation for day 70 were 5
Seroconversion: number of animals which produced a positive response (2.5 × background value) in each group

EXAMPLE 4

Preparation of *Bordetella pertussis* Filamentous Haemagglutinin/pertussis Toxin (toxoid)/chitosan Glutamate Composition 4A. A solution of 2% (20 mg/ml) chitosan glutamate (CSN) was prepared by dissolving 200 mg chitosan in 10 ml water.

4B *Bordetella pertussis* filamentous haemagglutinin (FHA), obtained from CAMR, Salisbury, Wiltshire, United Kingdom, was concentrated using an Aquacide II column and made up in phosphate buffered saline (PBS) to give a protein concentration of 267 μg/ml. Pertussis toxin (PT), non-toxic mutant, obtained from IRIS, Siena, Italy was concentrated using an Aquacide II column and made up in 0.5 M sodium chloride to give a final concentration of 267 μg/ml. Equal volumes of these two antigen solutions were mixed to give a solution containing each antigen at a final protein concentration of 133 μg/ml.

4C A 1:3 mixture of 2% CSN solution and FHA/PT solution was prepared to give an intranasal vaccine contain- Group 1: 20 μ(10 μl per nostril) FHA/PT/CSN solution administered intranasally. (FHA dose=2 μg, PT dose=2 μg, chitosan dose=100 μg)

Group 2: 20 μl (10 μl per nostril) PT/FHA solution administered intranasally. (FHA dose=10 μg, PT dose=2 μg)

Group 3: 20 μl (10 μl per nostril) CSN solution administered intranasally (CSN dose=100~g)

Group 4: 200 μl FHA/PT/Alhydrogel mixture administered intraperitoneally. (FHA dose=2 μg, PT dose=2 μg, Alhydrogel=40 μg)

Immunisation and Sampling Regime

4D The immunisation procedure was carried out twice at a monthly interval. The immunisation and sampling regime is shown in Table 6.

4E Five mice from each group at sampling points 1 and 2 were terminally bled by cardiac puncture. After collection of blood samples the animals were killed with an intravenous overdose of pentobarbitone sodium and the nasal passages and the lungs were respectively ravaged with 1 ml PBS containing 1% bovine serum albumin.

TABLE 6

| Immunisation | Day | Sample | Day |
|---|---|---|---|
| 1 | 1 | 1 | 28 |
| 2 | 28 | 2 | 42 |

Antibody Analysis

4F Anti-FHA IgG, anti-PT IgG antibodies in the serum samples and anti-FHA secretory IgA, anti-PT secretory IgA antibodies in the nasal wash and lung lavage samples were measured by Enzyme Linked Immunosorbant Assay (ELISA). The test samples were appropriately diluted with the sample buffer to four different concentrations and analysed in duplicate for each antibody. Titration curves were produced, the y-axis value was fixed at 2.5 times the background value and the interpolation value for each sample was calculated using the Kineticalc programme KC3. The geometric mean titration (GMT) value for each sample was then obtained by calculating the inverse of the interpolation value.

Results

4G The GMT values, for both anti-FHA and anti-PT serum IgG antibodies (Tables 7, 8 and FIG. 5*a*) show that the intranasally administered FHA/PT/chitosan composition (Group 1) elicited a primary systemic response and a considerably enhanced secondary response. In comparison, the nasally administered FHA/PT solution (Group 2) also elicited some primary systemic response and an enhanced secondary response. However the secondary responses to both FHA and PT produced by Group 1 were approximately 5 fold higher than the corresponding responses produced by Group 2.

Figure 5A:
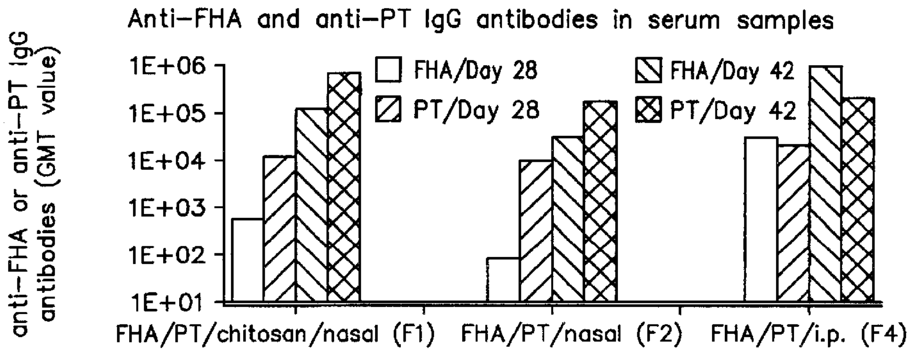
FIGS. 5*a*, 5*b*, and 5*c* illustrate the anti-FHA and anti-Pertussis toxin (toxoid; anti-PT) serum IgG response, lung lavage secretory IgA response and the nasal wash secretory IgA response, respectively, in mice immunized with FHA and PT.

4H As expected, the intraperitoneally administered FHA/PT solution (Group 4) elicited high primary and secondary responses to FHA and PT (Tables 7, 8 and FIG. 5A). However, the secondary responses to PHA and PT were approximately 30 and 10 fold higher than the primary responses respectively. The negative control group serum samples (Group 3) were found to be negative both for anti-FHA and anti-PT IgG antibodies (Tables 7, 8).

Figure 5B:
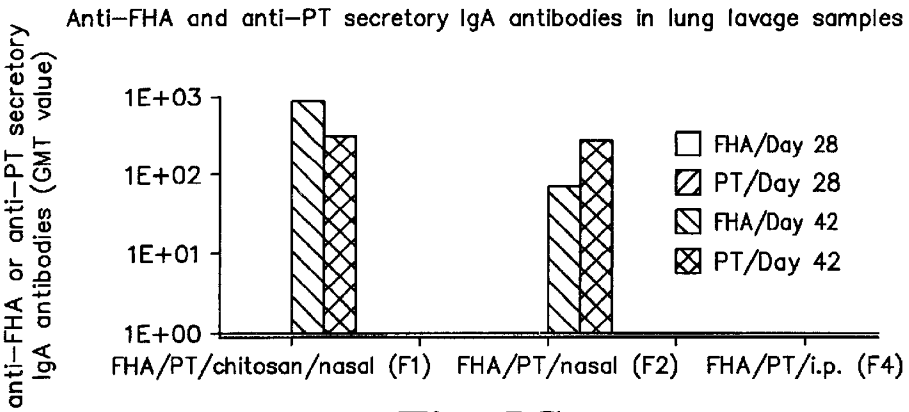

4I The GMT values for secretory IgA antibodies in the lung lavages (Tables 7, 8 and FIG. 5*b*) clearly show that both the nasal compositions FHA/PT/chitosan (Group 1) and FHA/PT (Group 2) elicited a secondary response to FHA and PT but neither antigen produced a primary response. The secondary responses to PT produced by Group 1 and Group 2 were similar, whereas this response to FHA produced by Group 1 was approximately 15 fold higher than the response to FHA produced by Group 2.

Figure 5C:
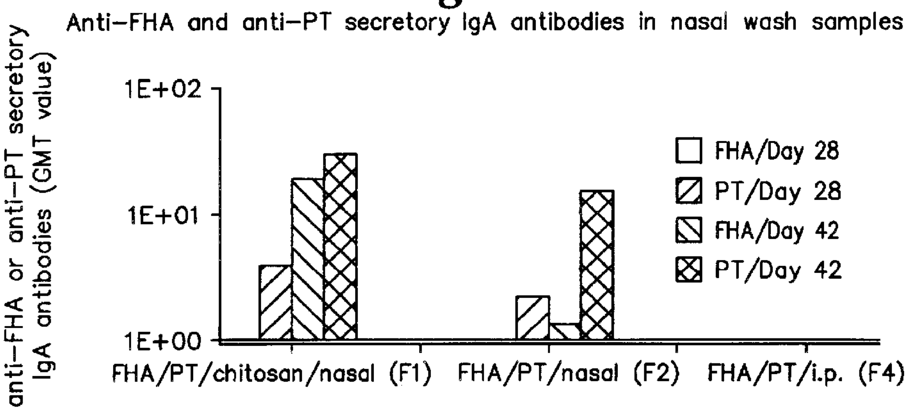

4J The GMT values for secretory IgA antibodies in the nasal washes (Tables 7, 8 and FIG. 5*c*) also show that both the nasal compositions in Group 1 and Group 2 elicited a secondary response to both the antigens, but only PT produced a small primary response. The secondary response to FHA produced by Group 1 was almost 15 fold higher than that produced by Group 2, whereas the corresponding response to PT produced by Group 1 was only twice as much as that produced by Group 2.

4K The lung lavage and nasal wash samples from the chitosan control group (Group 3) were found to be negative both for anti-PHA and anti-PT IgA antibodies (Tables 7, 8). The intraperitoneally administered FHA/PT/Alhydrogel (Group 4) was also found to produce no mucosal response (IgA antibodies) to either antigen in the lung lavage or the nasal washes.

TABLE 2

Summary of Geometric mean titration (GMT) values of anti-FHA serum IgG and anti-FHA secretory IgA (lung lavage and nasal wash) antibodies after the intraperitoneal or nasal administration of FHA (2 μg/mouse) and PT (2 μg/mouse) in various solution formulations in mice

| | Serum anti-FHA IgG | | | Lung larvage anti-FHA IgA | | | Nasal wash anti-FHA IgA | | |
|---|---|---|---|---|---|---|---|---|---|
| Formulation | Seroconversion | Mean GMT value | SD | Seroconversion | Mean GMT value | SD | Seroconversion | Mean GMT value | SD |
| Day 28 | | | | | | | | | |
| FHA/PT/chitosan/nasal (Group 1) | 4 out of 5 | 499.5 | 388.1 | 0 out of 5 | 0.0 | 0.0 | 0 out of 5 | 0.0 | 0.0 |
| FHA/PT/nasal (Group 2) | 3 out of 5 | 77.8 | 83.6 | 0 out of 5 | 0.0 | 0.0 | 0 out of 5 | 0.0 | 0.0 |
| chitosan/nasal (Group 3) | 0 out of 5 | 0.0 | 0.0 | 0 out of 5 | 0.0 | 0.0 | 0 out of 5 | 0.0 | 0.0 |
| FHA/PT/i.p. (Group 4) | 4 out of 4 | 25140.2 | 13690.5 | 0 out of 4 | 0.0 | 0.0 | 0 out of 4 | 0.0 | 0.0 |
| Day 42 | | | | | | | | | |
| FHA/PT/chitosan/nasal (Group 1) | 5 out of 5 | 118257.4 | 59051.0 | 4 out of 5 | 926.7 | 882.9 | 5 out of 5 | 19.6 | 14.1 |
| FHA/PT/nasal (Group 2) | 4 out of 5 | 25579.6 | 41735.6 | 2 out of 5 | 62.8 | 88.4 | 1 out of 5 | 1.3 | 2.9 |
| chitosan/nasal (Group 3) | 0 out of 5 | 0.0 | 0.0 | 0 out of 5 | 0.0 | 0.0 | 0 out of 5 | 0.0 | 0.0 |
| GHA/PT/i.p. (Group 4) | 5 out of 5 | 869421.2 | 419236.5 | 0 out of 5 | 0.0 | 0.0 | 0 out of 5 | 0.0 | 0.0 |

Seroconversion: number of animals which produced a positive response (2.5 × background optical density) in each group

TABLE 8

Summary of Geometric mean titration (GMT) values of anti-PT serum IgG and anti-PT secretory IgA (lung lavage and nasal wash) antibodies after the intraperitoneal or nasal administration of FHA (2 μg/mouse) and PT (2 μg/mouse) in various solution formulations in mice

| | Serum anti-PT IgG | | | Lung larvage anti-PT IgA | | | Nasal wash anti-PT IgA | | |
|---|---|---|---|---|---|---|---|---|---|
| Formulation | Seroconversion | Mean GMT value | SD | Seroconversion | Mean GMT value | SD | Seroconversion | Mean GMT value | SD |
| Day 28 | | | | | | | | | |
| FHA/PT/chitosan/nasal (Group 1) | 5 out of 5 | 11471.1 | 7875.0 | 0 out of 4 | 0.0 | 0.0 | 4 out of 5 | 3.9 | 4.5 |
| FHA/PT/nasal (Group 2) | 5 out of 5 | 8794.4 | 10759.4 | 1 out of 5 | 0.2 | 0.5 | 3 out of 5 | 2.2 | 2.4 |
| chitosan/nasal (Group 3) | 0 out of 5 | 0.0 | 0.0 | 0 out of 5 | 0.0 | 0.0 | 0 out of 5 | 0.0 | 0.0 |
| FHA/PT/i.p. (Group 4) | 4 out of 4 | 19269.3 | 14648.3 | 0 out of 4 | 0.0 | 0.0 | 0 out of 4 | 0.0 | 0.0 |
| Day 42 | | | | | | | | | |
| FHA/PT/chitosan/nasal (Group 1) | 5 out of 5 | 667556.6 | 748959.0 | 5 out of 5 | 315.3 | 262.2 | 5 out of 5 | 29.2 | 9.7 |
| FHA/PT/nasal (Group 2) | 5 out of 5 | 147081.3 | 134929.0 | 4 out of 5 | 254.7 | 485.1 | 5 out of 5 | 14.9 | 6.6 |
| chitosan/nasal (Group 3) | 0 out of 5 | 0.0 | 0.0 | 0 out of 5 | 0.0 | 0.0 | 0 out of 5 | 0.0 | 0.0 |
| FHA/PT/i.p. (Group 4) | 5 out of 5 | 220118.2 | 83448.9 | 0 out of 3 | 0.0 | 0.0 | 0 out of 5 | 0.0 | 0.0 |

Seroconversion: number of animals which produced a positive response (2.5 × background optical density) in each group

We claim:

1. A vaccine composition for intranasal administration, wherein the composition comprises antigen and an effective adjuvant amount of a chitosan, wherein the chitosan is produced from chitin by deacetylation to a degree of greater than 40% deacetylation and has a molecular weight between 10 kD and 500 kD.

2. The composition of claim 1 wherein the antigen is selected from the group consisting of a protein, a recombinant protein, a glycoprotein, and a peptide.

3. The composition of claim 1 wherein the antigen is selected from the group consisting of a *Bordetella pertussis* antigen, a meningococcal antigen, a tentanus antigen, a diptheria antigen, a pneumococcal antigen, a tuberculosis antigen, and a RSV antigen.

4. The composition of claim 1 wherein the composition induces tolerance when administered.

5. The composition of claim 1 wherein the antigen is in a purified form.

6. The composition of claim 1 wherein the concentration of the chitosan is between about 0.02% and 10%.

7. The composition of claim 6 wherein the concentration of the chitosan is between about 0.1% and 5%.

8. The composition of claim 7 wherein the concentration of the chitosan is between about 0.25% and 2%.

9. The composition of claim 1 wherein the chitosan is water soluble.

10. The composition of claim 1 wherein the degree of deacetylation is between 50% and 90%.

11. The composition of claim 1 wherein the degree of deacetylation m between 70% and 95%.

12. The composition of claim 1 wherein the molecular weight of the chitosan is between about 50 kD and 300 kD.

13. The composition of claim 12 wherein the molecular weight of the chitosan is between about 100 kD and 300 kD.

14. The composition of claim 1 wherein the pH of the composition is between about 5.5 and 6.5.

15. The composition of claim 14 wherein the pH is approximately 6.

16. The composition of claim 1 formulated as a dry powder.

17. The composition of claim 1 in the form of microspheres.

* * * * *